United States Patent [19]

Finkelstein et al.

[11] Patent Number: 4,744,751

[45] Date of Patent: May 17, 1988

[54] REMOVEABLE FIXTURE FOR DENTAL ARTICULATORS

[76] Inventors: Arthur M. Finkelstein; Reuben W. Finkelstein, both of 2170 Brigham St., Brooklyn, N.Y. 11229

[21] Appl. No.: 825,016

[22] Filed: Jan. 31, 1986

[51] Int. Cl.[4] .............................................. A61C 11/00
[52] U.S. Cl. ...................................... 433/60; 433/63; 433/65
[58] Field of Search ........................ 433/60, 54, 63, 65

[56] References Cited

U.S. PATENT DOCUMENTS

| | | | |
|---|---|---|---|
| 537,812 | 4/1895 | Bragg | 433/60 |
| 654,109 | 7/1900 | Backstrom | 433/60 |
| 981,430 | 1/1911 | Kennedy | 433/60 |
| 1,271,161 | 7/1918 | Hall | 433/60 |
| 1,485,657 | 3/1924 | Williams | 433/60 |
| 1,736,006 | 11/1929 | Hagman | 433/60 |
| 2,070,025 | 2/1937 | Phillips | 433/60 |
| 2,621,407 | 12/1952 | Schlesinger | 433/60 |
| 2,765,533 | 10/1956 | McMorris | 433/60 |
| 3,975,489 | 8/1976 | Mercer | 264/222 |
| 4,030,197 | 6/1977 | Linck | 433/60 |
| 4,128,942 | 12/1978 | Schleich | 433/65 |
| 4,169,314 | 10/1979 | Mercer et al. | 433/60 |
| 4,358,269 | 11/1982 | Hay et al. | 433/60 |
| 4,371,338 | 2/1983 | Mercer et al. | 433/60 |
| 4,501,556 | 2/1985 | Zelnigher | 433/60 |

OTHER PUBLICATIONS

Zahn Dental Co., Inc. Catalogue, Spring 1984, pp. 10-13.
Teledyne Dental Catalogue-Hanau Division 1976, pp. 3-13.
Dental Laboratory Discount Supply Catalogue, Spring-Summer, 1984, pp. 16-17.
Henry Schein, Inc. Dental Catalogue, 1977, pp. 154-155.
Henry Schein, Inc. Dental Catalogue, Spring/Summer 1985, pp. 234-235.

Primary Examiner—John J. Wilson
Attorney, Agent, or Firm—Pennie & Edmonds

[57] ABSTRACT

Apparatus for removably mounting dental casts within a dental articulator. The apparatus includes two removable fixtures attached to the articulator by a connector such as a screw, bolt or threaded rod; each fixture having a plate for supporting a dental cast, a groove and pin arrangement for orienting the fixture within the articulator and at least two brackets, each provided with apertures for passing a retaining bolt which maintains the cast in a predetermined position. Also, a method for removably and reproducibly mounting dental casts within a dental articulator by using the removable fixtures of the invention.

14 Claims, 5 Drawing Sheets

REMOVEABLE FIXTURE FOR DENTAL ARTICULATORS

FIELD OF THE INVENTION

The invention relates to an apparatus and method for mounting and adjusting the spatial orientation of paired dental casts in such a manner as to facilitate their removal and remounting in a reproducible position upon a dental articulator.

BACKGROUND OF THE INVENTION

The facilitation of the removal and remounting of dental casts upon a dental articulator in a standardized and reproducible manner is important and necessary to those engaged in the fabrication of dental prostheses. The ability to remount a dental cast which has been removed from the articulator to its original position is especially useful in situations where it is desired to use a specific articulator for several pairs of dental casts at the same time.

With respect to the prior art, dental articulators are a common and necessary apparatus utilized in the fabrication of dental prostheses and are well-known in the art. In order to construct such a prosthesis, the dentist takes impressions of the patient's maxillary and mandibular arches. Theses arches may or may not still include some of the patient's natural teeth. The impressions provide negative imprints of the arches and serve as the molds into which the raw material for forming positive dental casts are poured. These positive casts then serve as a template upon which the prosthesis may be constructed.

The dental casts are then mounted upon a device known as a dental articulator in order to facilitate construction of the prosthesis. This device allows the maxillary (upper) and mandibular (lower) casts to be maintained in the same anatomical relationship as in the mouth of the patient while the dentist fabricates the appliance. This is true in all cases, even those where only one arch is to receive a prosthesis, since the prosthesis must also conform with the related surfaces on the other arch in the patient's mouth.

A further reason for mounting the positive dental casts on an articulator is to permit the arrangement of any false teeth into a proper position for occlusion. In the case of partial dentures, the denture teeth must correctly occlude with the remaining natural teeth. With full dentures, greater tolerances are permitted in order to improve both function and aesthetics.

To obtain the correct occlusion, the dentist must account for not only the vertical bite but must also allow for a degree of lateral movement as well as anterior and posterior movement of the lower jaw. Many dental articulators are constructed in a manner allowing the dentist to simulate these movements to a great degree, thus improving the fit of the prosthesis.

The most common technique for attaching the dental casts in the articulator has been to mount them on a support plate with plaster, which is usually a gypsum—based material. In the event that the cast must be removed, the plaster "joint" must be broken, and the cast must later be remounted. It is difficult to precisely remount the cast in its previous orientation. Thus, much of the orientation and alignment procedure would have to be repeated.

A further disadvantage of this technique is that it is relatively expensive, dusty and time consuming to mount the dental casts with plaster. The powdered plaster must first be thoroughly mixed with a liquid such as water and the plaster must then be allowed time in which to set. This process is subject to error because, once the plaster has set, the orientation of the casts may not be changed without destroying the bond, as mentioned above.

Most dental articulators built to date utilize the plaster mounting techniques described above. Several experimental versions have been constructed using mechanical mounting devices such as claws or other clamping devices to supplant the use of plaster as a mounting material. In some cases, dental casts have been provided with grooves for engagement with projections located upon the articulator to facilitate removal and remounting, but there is no direct evidence that this arrangement materially assists the dentist by instilling a greater degree of reproducibility into the remounting process. For example, U.S. Pat. No. 4,169,314 discloses a dental articulator for mounting dental casts by means of a screw engaging a threaded aperture embedded into the base of the cast. Such fixed location points are not disturbed by the retaining means of the articulator and therefore permit a more reproducible reorientation of the casts during any subsequent remounting.

U.S. Pat. No. 4,371,338 describes a dental articulator having protruding locating pins for entering a fixed, unthreaded aperture in the base of both dental casts. These apertures are easier and faster to form, by means of a dental lathe, than the threaded apertures of the type described in U.S. Pat. No. 4,196,314. One aperture is preferably a round aperture in the central portion of the dental cast and the second aperture is preferably a radial slot. Each aperture receives a locating pin which protrudes from the articulator. The central pin prevents all movement of the cast except rotational movement while the pin engaging the radial aperture prevents even the rotational movement of the cast.

With the exception of articulators of the type described above, prior art articulators which eschew the use of plaster favor mechanical mounting devices. Such mechanical devices perform their intended function by acting as a clamp around the periphery of the dental casts. A serious drawback to the use of these devices, however, is their inability to reproducibly reorient a dental cast which has been removed from the articulator when remounting it later for further work. As the plaster of which the casts are made is mechanically abraded by the clamps, the dental cast tends to wobble or shift in position. Reproducibility is an absolute requirement for the fabrication of dental prostheses except in the case of the more simple crown and bridge work.

The applicants have discovered a fixture and a method which will enhance the reproducibility of the orientation which may be attained upon removing and then remounting dental casts upon a prior art dental articulator which previously utilized the plaster mounting technique. The fixture is capable of engaging and positioning a paired dental cast in a predetermined orientation to facilitate the construction of a dental prosthesis and then re-positioning the cast at the exact same position when it is placed on a dental articulator for further work.

SUMMARY OF THE INVENTION

The invention relates to an apparatus for reproducibly mounting and adjusting the position of a pair of dental casts upon a dental articulator which comprises two removable fixtures. Each of the fixtures comprises support means having opposed first and second surfaces, means for removably attaching the support means to a dental articulator, means for retaining a dental cast in a predetermined position upon the fixture, and registration means for orienting the fixture within a dental articulator. The retaining means is preferably located upon the second surface of the support means, while the registration means is preferably located upon the first surface of the support means. The lower fixture may also include means for adjusting the vertical position of its support means.

In the apparatus described above, the support means may be a plate and the registration means for orienting each fixture comprises at least one aperture located on the first surface of the support means for engaging a locating pin projecting in a substantially perpendicular direction from the dental articulator.

The registration means may further comprise an elongated groove in the first surface of the support means at a location 180° opposed from the first aperture for engaging a second locating pin on the articulator.

The apparatus is also provided with means for attaching the support means, such as a screw, bolt or threaded rod. The apparatus is further provided with retaining means which comprises a plurality of bracket means each adapted and configured to allow passage of orientation means through the bracket means and thereafter into a dental cast. The orientation means may preferably be a retaining bolt and the bracket means each contain a plurality of selectable aperture positions for insertion of the orientation means.

The invention therefore provides an apparatus for reproducibly mounting and adjusting the position of a pair of dental casts upon a dental articulator. This apparatus includes removable upper and lower fixtures, each fixture comprising a support plate, means for attaching the support plate to a dental articulator, a plurality of bracket means attached to and spaced along the periphery of the support plate, a plurality of cast retaining means each adjustable to engage and penetrate a portion of the dental casts, and registration means for orienting the support plate within the articulator. The registration means is preferably located on the bottom of the support plates and the lower fixture further comprises means for adjusting the vertical position of its support plate. The bracket means each include a plurality of apertures for engaging cast retaining means, and each cast retaining means includes means for preventing substantial penetration of the dental casts.

Applicants further disclose a method for removably and reproducibly mounting and adjusting the position of a pair of dental casts upon a dental articulator which comprises orienting an upper mounting fixture upon an upper portion of a dental articulator, attaching the upper mounting fixture to the articulator, orienting a lower mounting fixture upon a lower portion of the dental articulator, attaching the lower mounting fixture to the articulator, positioning a cast of a patient's maxillary arch upon the upper mounting fixture, retaining the maxillary cast upon the upper mounting fixture, positioning a cast of a patient's mandibular arch upon the lower mounting fixture, and retaining the mandibular cast upon the lower mounting fixture.

In the method described above, the upper and lower mounting fixtures are each oriented by inserting at least one locating pin projecting in a substantially perpendicular direction from the upper and lower portions of the dental articulator into a corresponding aperture located in a surface of each mounting fixture. The method as described above may further comprise inserting at least a second locating pin also projecting in a substantially perpendicular direction from the upper and lower portions of the dental articulator and parallel to the first mounting pin into an elongated groove on the surface of each mounting fixture.

With the method as described herein, the upper and lower mounting fixtures are each attached to the respective upper and lower portions of the dental articulator by inserting a screw or bolt through an aperture located substantially in the center of each fixture and thereafter into a frame portion in the respective upper and lower portions of the dental articulator.

The maxillary and mandibular dental casts are positioned and retained upon the upper and lower mounting fixtures respectively by inserting a retaining bolt through a preselected aperture in each of a plurality of bracket means which are located upon the upper and lower mounting fixtures and thereafter screwing said bolts into an outer surface of the maxillary and mandibular dental casts. Applicants' method for removeably and reproducibly mounting dental casts in a dental articulator therefore comprises making the removable fixtures according to the method described above, attaching one fixture to the upper portion of a dental articulator, attaching the second fixture to the lower portion of the dental articulator, and affixing a dental cast to each fixture.

BRIEF DESCRIPTION OF THE DRAWINGS

Further benefits and advantages of the invention will become apparent from a consideration of the following description given with reference to the accompanying drawing figures which specify and show preferred embodiments of the present invention, and wherein.

DETAILED DESCRIPTION OF THE PREFERRED EMBODIMENTS

Figure 1:
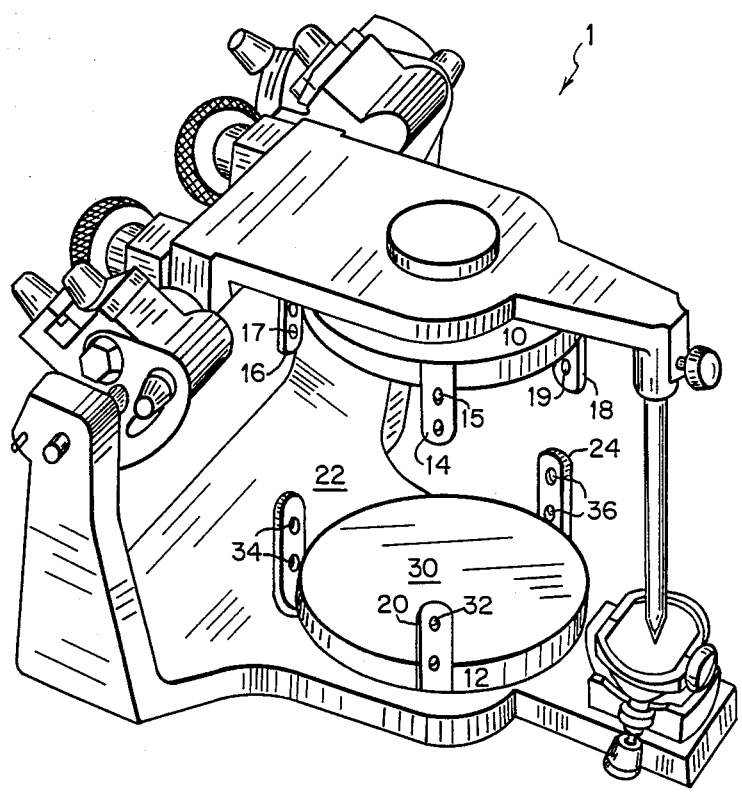
FIG. 1 is a perspective view of a dental articulator utilizing an upper and lower mounting fixture constructed according to the invention.

Referring to FIG. 1 there is illustrated dental articulator 1 having upper and lower mounting fixtures 10,12 for mounting and adjusting the spatial orientation of paired dental casts in such a manner as to facilitate their removal and subsequent remounting in a reproducible position. Upper mounting fixture 10 is equipped with mounting brackets 14,16,18 and lower mounting fixture 12 is provided with similar mounting brackets 20,22,24.

Figure 2:
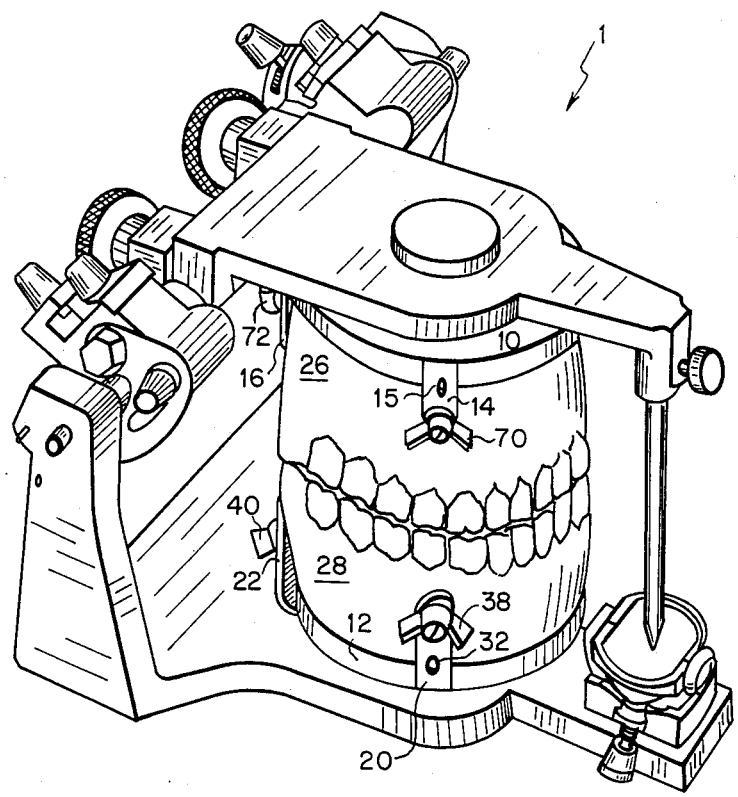
FIG. 2 is a perspective view of the dental articulator of FIG. 1 with a set of dental casts mounted upon the fixtures.

FIGS. 1 and 2 provide a perspective view of dental articulator 1. The mounting fixtures 10,12 of the invention are designed for use with any standard dental articulator which is used to mount dental casts by plaster bonding to a support plate. FIG. 2 illustrates the use of mounting brackets 14,20,22 for engaging the base of dental casts 26,28 to enable the dentist to reproducibly position these casts in the same anatomical relationship which they occupy in the patient's mouth while fabricating a dental prostheses. The remaining features of the dental articulator have not been described as they are well-known to those skilled in the art.

Figure 3:
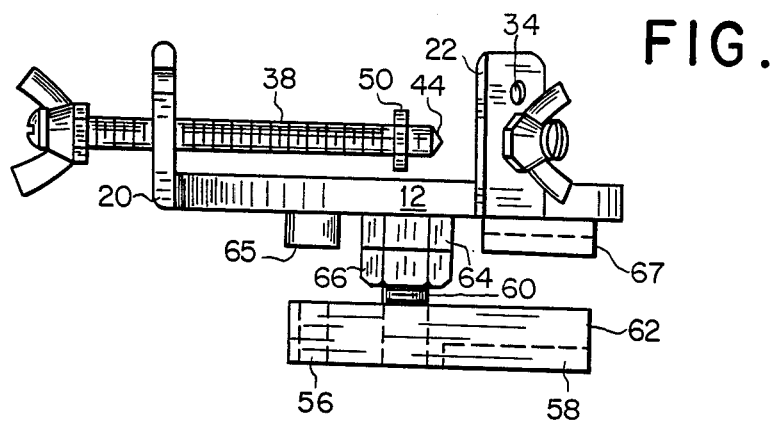
FIG. 3 is a side view of a lower mounting fixture of the invention.

FIG. 3 is a side view of lower mounting fixture 12, illustrating certain features of applicants' fixture which effect the attachment and movement of fixture 12 on dental articulator 1. Lower mounting fixture 12, is adapted and configured so as to provide registration means for a pair of perpendicular pins (not shown) located upon the lower frame of dental articulator 1. By registration means, applicants mean the aperture 56 and groove 58 which serve to locate and orient the mounting fixture(s).

One pin projects in a substantially perpendicular direction from the frame of dental articulator 1 into circular aperture 56 whereas the second pin can be received at any location along the length of groove 58, thus permitting flexibility in the adaptation of the fixture 12 into a number of articulators having slightly different positions for the second pin. To maintain the attachment of mounting fixture 12 to the frame of dental articulator 1, a threaded bolt 60 and a flat plate 62 is utilized. This arrangement is easily adapted for tightening by hand, but is not limiting of the invention since alternate arrangements, such as knurled surfaces, screw or hex-head bolts, and the like can also be utilized.

Bolt 60 passes through coupling nuts 64,66 before engaging threaded aperture 68 located in the center of lower mounting fixture 12. Rotation of nut 66 therefore permits the position of lower mounting fixture 12 to be varied either upwardly or downwardly. This is advantageous in that it enables a dentist working on a mounted cast to orient it in the proper position for occlusion. Lower mounting fixture 12 in FIG. 3 is also equipped with aperture 65 and groove 67 located directly upon the bottom surface of the fixture, which can serve as alternate registration means, thereby enabling fixture 12 to be utilized interchangably with upper mounting fixture 10 upon the removal of plate 62 and coupling nuts 64 and 66.

Figure 4:
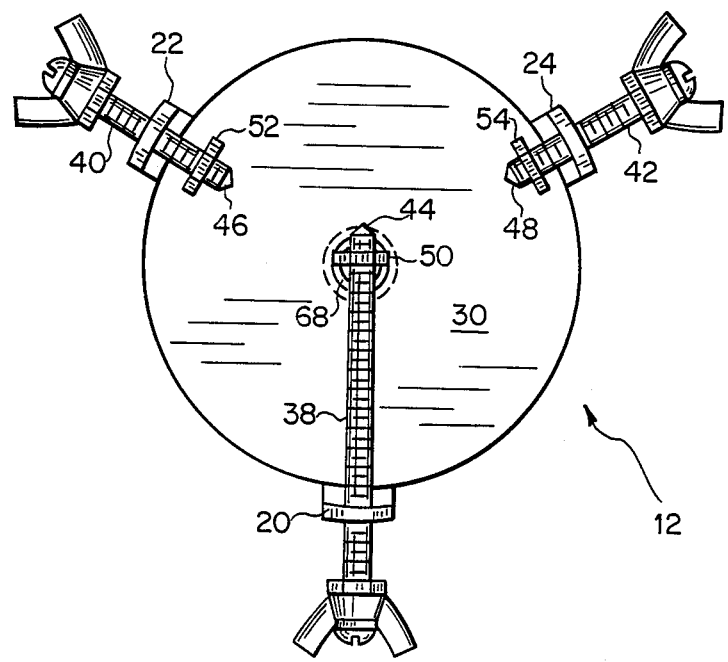
FIG. 4 is a plan view of the top surface of the lower mounting fixture illustrated in FIG. 3

Referring now to FIG. 4, there is illustrated the top surface 30 of lower mounting fixture 12. Along the periphery of lower fixture 12 are mounting brackets 20,22,24. These mounting brackets may be formed as part of mounting fixture 12 or they may be separately constructed and attached by means of bolts or rivets to the fixture. In alternate embodiments, they may be attached with the use of an adhesive or by welding.

As shown in FIG. 1, each of mounting brackets 20,22,24 contains a pair of apertures 32,34,36 through the surface perpendicular to the upper surface 30 of the mounting fixture 12. These apertures are preferably threaded for insertion and adjustment of threaded retaining bolts 38,40,42. Either the upper or lower set of apertures may be used, depending upon the size of the cast.

As illustrated in FIGS. 3 and 4, the terminal portion 44,46,48 of each retaining bolt 38,40,42 is pointed so as to enable it to be manually or mechanically screwed into the comparatively soft surface of dental cast 28 (not shown). Bolts 38,40,42 are also equipped with collar rings 50,52,54 located in a fixed position on the bolt. Once a retaining bolt is inserted through an aperture in a mounting bracket and screwed into the surface of the cast, the collaring prevents the operator from screwing the bolt too far into the cast, and thereby causing the cast to chip or break.

In an alternate embodiment, the position of these collar rings may be adjustable along the length of the retaining bolts so as to allow a dentist to screw the bolts more deeply into a larger cast that requires extra support. Also, although shown as wing head bolts, the retaining bolts 38, 40, 42 may also be constructed with screw or hex heads for operation with a screwdriver or the like, or they may have knurled surfaces for hand rotation.

With the use of applicant's mounting fixture, therefore, even after the dentist removes cast 28 from the mounting fixture 12 by loosening retaining bolts 38,40,42, the cast can always be easily and reproducibly remounted and reoriented by once again placing it between mounting brackets 20,22,24 and screwing threaded retaining bolts 38,40,42 into the same location on the cast to a depth defined by the location of the respective collar ring.

Figure 5:
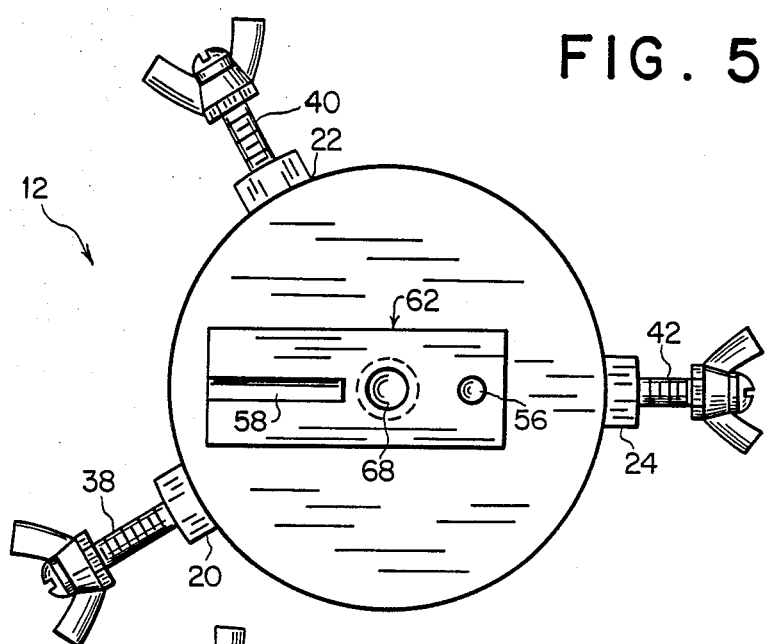
FIG. 5 is a plan view of the bottom surface of the lower mounting fixture illustrated in FIGS. 3 and 4.

FIG. 5 is a plan view of the bottom surface of lower mounting fixture 12 and illustrates in greater detail the registration means utilized by applicants to attach mounting fixture 12 to the base of dental articulator 1. As described above, threaded bolt 60 (not shown) passes through plate 62 and couples the mounting fixture 12 to the frame of the articulator 1 (not shown), by passing through the frame in a perpendicular direction and engaging the threaded aperture 68 in the center of fixture 12. In addition, two perpendicular pin members (not shown) project upwardly from the frame of the articulator 1 and engage aperture 56 and groove 58, thus allowing for a certain degree of lateral tolerance in the fit.

Figure 6:
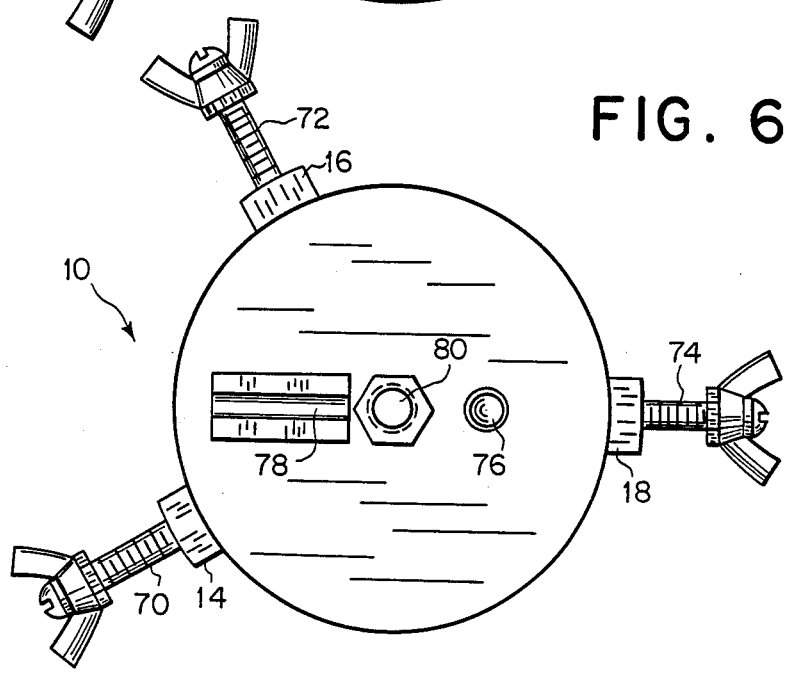
FIG. 6 is a plan view of the top surface of the upper mounting fixture.

FIG. 6 is a plan view of the top surface of upper mounting fixture 10 which is also affixed to the frame of the articulator 1 in a horizontal plane, parallel to the surface of lower mounting fixture 12. Along the periphery of upper mounting fixture 10 are located mounting brackets 14,16,18 each having a pair of apertures 15,17,19, through the surface of the bracket perpendicular to the lower surface of the mounting fixture. Mounting brackets 14,16,18 may be formed as part of fixture 10 as they may be attached to fixture 10 as described above for brackets 20,22,24.

In order to mount cast 26 to upper mounting fixture 10, a procedure identical to that for mounting cast 28 to lower fixture 12 is followed. A number of threaded retaining bolts 70,72,74 are inserted through one set of apertures 15,17,19 in upper mounting brackets 14,16,18. The pointed ends of these bolts are then screwed into the comparatively soft surface of dental cast 26 to a distance determined by the fixed or movable location of a collar ring which is located on each retaining bolt.

Upper mounting fixture 10 is attached to the frame of the dental articulator 1 in much the same manner as lower fixture 12. Registration means, similar to those located upon the bottom surface of lower mounting fixture 12, are located on the top surface of mounting fixture 10 for this purpose. A pair of mounting pins (not shown) extend downwardly in a substantially perpendicular direction from the frame of articulator 1.

One pin lockingly engages aperture 76 while the second pin is inserted at a location along the length of groove 78 which is conducive to the variable location of these pins on the frame of dental articulator 1 as constructed by different manufacturers. To secure mounting fixture 10 to the frame of articulator 1 a threaded bolt (not shown) is inserted downwardly through the frame of articulator 1 and into threaded aperture 80 located in the center of mounting fixture 10.

Figure 7:
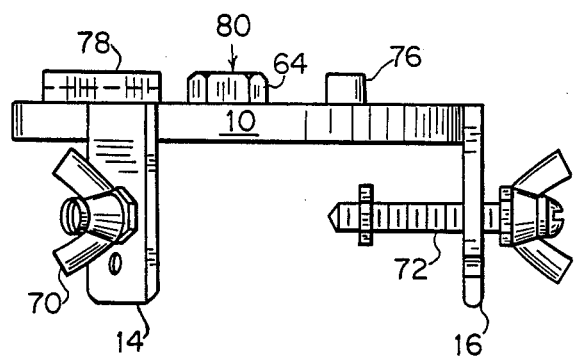
FIG. 7 is a side view of the upper mounting fixture illustrated in FIG. 6.

FIG. 7 is a side view of the upper mounting fixture 10 which illustrates the similarities between it and lower fixture 12. An important difference between the two fixtures, however, is that lower fixture 12 is vertically adjustable by rotating coupling nut 66 to move the fixture either upwardly or downwardly, depending on whether the rotation of the coupling nut is clockwise or counterclockwise. This enables a dentist who utilizes one dental articulator to work on dental casts of various sizes to move the lower cast so as to obtain the proper position for occlusion, no matter what the difference in mouth size, from one patient to the next. Upper mounting fixture 10 can also be provided with the feature, however, in the ordinary arrangement it is not necessary. The coupling nut 64 is shown as a hexagonal nut for rotation by a wrench or other suitable tool. It is possible that this nut 64 can be provided as a ring having a knurled periphery to allow for adjustment by hand.

While it is apparent that the invention herein disclosed is well calculated to achieve the desired results it will be appreciated that numerous modifications and embodiments may be devised by those skilled in the art and it is intended that the appended claims cover all such modifications and embodiments as fall within the true spirit and scope of the present invention.

We claim:

1. An apparatus for reproducibly mounting and adjusting the position of a pair of dental casts upon a dental articulator which comprises removable upper and lower fixtures, each fixture comprising:
    a support plate;
    means for attaching said support plate to a dental articulator;
    a plurality of bracket means attached to and spaced along the periphery of said support plate, said bracket means each including a plurality of apertures for engaging cast retaining means;
    a plurality of cast retaining means each adjustable to engage and penetrate a portion of said dental casts, said cast retaining means including adjustable means for contacting said dental casts to provide a limited predetermined depth of penetration thereof, whereby said dental casts may be reproducibly positioned upon said support plate by adjusting and advancing said cast retaining means to penetrate said dental casts to said predetermined depth; and
    registration means for orienting said support plate within said articulator, said registration means located on the bottom of said support plate;
    said lower fixture further comprising means for adjusting the vertical position of its support plate with respect to the articulator.

2. The apparatus of claim 1 wherein the registration means is at least one aperture located on the bottom of said support plate for engaging a locating pin projecting from said dental articulator.

3. The mounting apparatus of claim 2 wherein said registration means further comprises an elongated groove on the bottom of said support plate at a location 180° opposed from said at least one aperture for engaging a second locating pin projecting from said dental articulator.

4. The apparatus of claim 1 wherein said means for attaching said support plate to said dental articulator is a screw, bolt or threaded rod.

5. The apparatus of claim 2 wherein each of said cast retaining means comprises a threaded elongated member for engaging an aperture of said bracket means, said member having a forward end and tip for penetration of said dental casts and a collar ring movable to various positions upon and located on said forward end spaced from said tip for contact with said dental casts to provide said limited predetermined depth of penetration thereof.

6. An apparatus for reproducibly mounting and adjusting the position of a pair of dental casts upon a dental articulator which comprises removable upper and lower fixtures, each fixture comprising:
    a support plate;
    means for attaching said support plate to a dental articulator;
    a plurality of bracket means attached to and spaced along the periphery of said support plate, said bracket means each including at least one aperture for engaging cast retaining means;
    a plurality of cast retaining means each adjustable to engage and penetrate a portion of said dental casts, said cast retaining means including adjustable means for contacting said dental casts to provide a limited predetermined depth of penetration thereof, whereby said dental casts may be reproducibly positioned upon said support plate by adjusting and advancing said cast retaining means to penetrate said dental casts to said predetermined depth; and
    registration means for orienting said support plate within said articulator, said registration means located on the bottom of said support plate;
    at least one of said fixtures further comprising means for adjusting the vertical position of its support plate with respect to the articulator.

7. The apparatus of claim 6 wherein said bracket means each contain a plurality of apertures in selectable positions for engaging said cast retaining means.

8. The apparatus of claim 6 wherein the registration means is at least one aperture located on the bottom of said support plate for engaging a locating pin projecting from said dental articulator.

9. The mounting apparatus of claim 8 wherein said registration means further comprises an elongated groove on the bottom of said support plate at a location 180° opposed from said at least one aperture for engaging a second locating pin projecting from said dental articulator.

10. The apparatus of claim 6 wherein said means for attaching said support plate to said dental articulator is a screw, bolt or threaded rod.

11. The apparatus of claim 6 wherein each of said cast retaining means comprises a threaded elongated member for engaging an aperture of said bracket means, said member having a forward end and tip for penetration of said dental casts and a collar ring movable to various positions upon and located on said forward end spaced from said tip for contact with said dental casts to provide said limited predetermined depth of penetration thereof.

12. An apparatus for reproducibly mounting and adjusting the position of a pair of dental casts upon a dental articulator which comprises removable upper and lower fixtures, each fixture comprising:

a support plate;

means for attaching said support plate to a dental articulator;

a plurality of bracket means attached to and spaced along the periphery of said support plate, said bracket means each including at least one aperture for engaging cast retaining means;

a plurality of cast retaining means each adjustable to engage and penetrate a portion of said dental casts, said cast retaining means including adjusting means for contacting said dental casts to provide a limited predetermined depth of penetration thereof, whereby said dental casts may be reproducibly positioned upon said support plate by adjusting and advancing said cast retaining means to penetrate said dental casts to said predetermined depth; said cast retaining means each consisting essentially of a threaded elongated member for engaging an aperture of said bracket means, said member having a forward end and tip for penetration of said dental casts; means for rotation of said cast retaining means for advancing or withdrawing said forward end and tip towards and away from said dental casts; and said adjustable means of said cast retaining means being in the form of a collar ring movable to various positions upon and located on said forward end spaced from said tip for contact with said dental casts to provide said predetermined limited depth of penetration thereof;

registration means for orienting said support plate within said articulator, said registration means located on the bottom of said support plate and comprising at least one aperture and one elongated groove each located on the bottom of said support plate for engaging first and second locating pins projecting from said dental articulator, said groove being positioned and located 180° opposed from said aperture; and at least one of said fixtures further comprising means for adjusting the vertical position of its support plate with respect to the articulator.

13. The apparatus of claim 12 wherein said bracket means each contain a plurality of apertures in selectable positions for engaging said cast retaining means.

14. The apparatus of claim 12 wherein said means for attaching said support plate to said dental articulator is a screw, bolt or threaded rod.

* * * * *